United States Patent [19]
Broicher et al.

[11] Patent Number: 5,410,154
[45] Date of Patent: Apr. 25, 1995

[54] DEVICE FOR DETECTING QUALITY ALTERATIONS IN BULK GOODS TRANSPORTED ON MOVING BELT CONVEYORS

[76] Inventors: Heribert F. Broicher, Bergtal 7A, 38640 Goslar; Arthur Zydek, Strobenstr. 2, 38312 Gross Flöthe, both of Germany

[21] Appl. No.: 211,953

[22] PCT Filed: Oct. 30, 1992

[86] PCT No.: PCT/EP92/02483
§ 371 Date: May 6, 1993
§ 102(e) Date: May 6, 1994

[87] PCT Pub. No.: WO93/10436
PCT Pub. Date: May 27, 1993

[30] Foreign Application Priority Data
Nov. 11, 1991 [DE] Germany ............ 41 37 008.2

[51] Int. Cl.⁶ .............. G01N 21/01; G01N 21/17; G01N 21/62
[52] U.S. Cl. .............. 250/339.05; 250/339.01; 250/359.1; 250/341.1
[58] Field of Search .......... 250/339.01, 339.05, 250/359.1, 910, 372, 458.1, 341.1, 341.7, 341.8, 339.11

[56] References Cited
U.S. PATENT DOCUMENTS
3,761,715  9/1973  Menzies ............... 250/338.5
3,806,730  4/1974  Tirkkonen et al. ..... 250/359.1 X
4,450,356  5/1984  Murray et al. ........ 250/338.5 X
4,785,185 11/1988  Izatt et al. .......... 250/359.1 X
4,959,549  9/1990  Haub et al. .

FOREIGN PATENT DOCUMENTS
0336235  3/1989  European Pat. Off. .
0345949  5/1989  European Pat. Off. .
59-120940  7/1984  Japan ............... 250/341.8
61-4946  1/1986  Japan ............... 250/341.1
62-85845  4/1987  Japan ............... 250/341.1

OTHER PUBLICATIONS
Patent Abstracts of Japan, vol. 13, No. 492 (P-555), Nov. 8, 1989, JP 1196536.
Patent Abstracts of Japan, vol. 14, No. 303 (P-1070), Jun. 29, 1990, JP 2096638.

*Primary Examiner*—Constantine Hannaher
*Assistant Examiner*—Edward J. Glick
*Attorney, Agent, or Firm*—Shlesinger, Arkwright, & Garvey

[57] ABSTRACT

A device for detecting quality alterations in bulk goods transported on moving belt conveyors comprising a pulsed, monochromatic light source (1), frequency multipliers (2) and dichroic mirrors (3) or prisms to simultaneously generate several light beams having different wavelengths and irradiate several spots (6) of the flow of bulk goods on the belt conveyor (7). In addition, a detector unit is provided for observing the irradiated spots (6) in the flow of bulk goods for measuring excited photoluminescence, reflected light and temperatures, as well as for carrying out signal analysis with time resolution. The triggering of the device is adapted to the running speed of the belt conveyor (7) and allows the same area of the moving flow of the bulk goods to be irradiated several times in the spots (6) with beams having different wavelengths. The signal analysis includes detecting signal intensity and the fading behaviour of the signals in defined spectral ranges. The device does not affect operation of the belt conveyor but makes possible the control of subsequent devices.

10 Claims, 1 Drawing Sheet

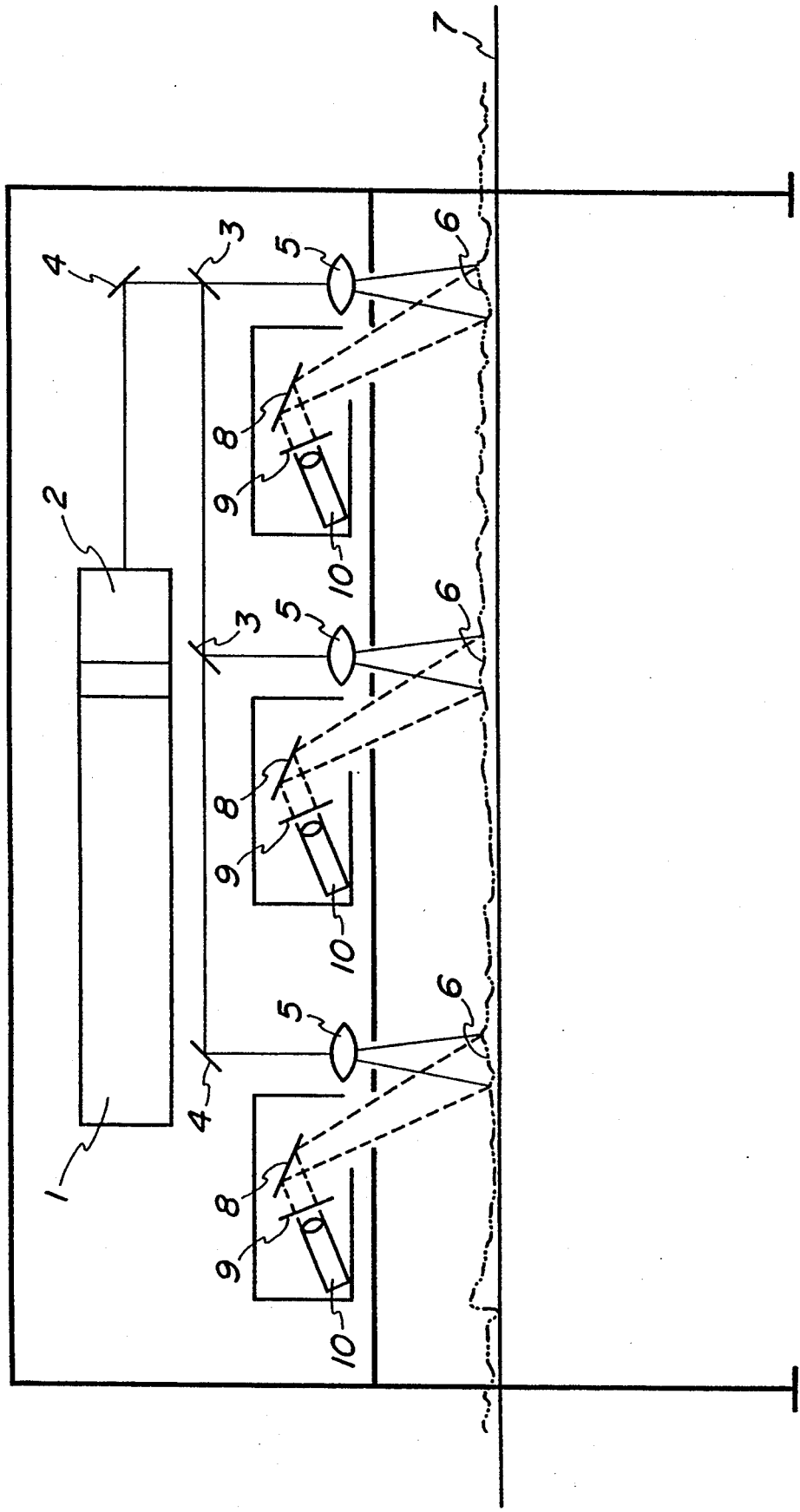

DEVICE FOR DETECTING QUALITY ALTERATIONS IN BULK GOODS TRANSPORTED ON MOVING BELT CONVEYORS

BACKGROUND OF THE INVENTION

1. Field of the Invention

The present invention relates to a device for detecting quality alterations in bulk goods on moving belt conveyors.

2. Description of the Prior Art

Through a publication by SYMONDS, D. F., 1991, "On-Line Ash Analysers Improve US Efficiency", MINTECH '91, pages 163 ff, Sterling Publications International Limited, London a device for determination of the ash content of bulk coal on belt conveyors is known, which by means of gamma ray absorption and backscatter measures the density of the material and, thus, indirectly the ash content of the coal. Devices of this kind have been marketed for more than 25 years by various manufacturers, as e.g. by the company "Laboratorien Prof. Dr. Berthold GmbH und Co.", Wildbad, Germany.

Analytically, these devices are hampered by measuring the density of a mixture of different matter only and, thus, can indicate indirectly only the amount of a certain component in simple mixtures.

The Finnish company "Outokumpu Electronics Oy" also markets devices of said kind, where the type "Beltcon 100" operates with gamma rays, while the type "Beltcon 200" is based on X-rays. The technical paper "Mining Journal", London, UK covered these devices in its issue of May 1991.

In general all above mentioned devices, which operate with gamma rays or X-ray fluorescence, have the disadvantage, that the radioactive sources used pose a health risk during maintenance and transport and that after their useful life have to be disposed of.

Devices for the determination of quality parameters of bulk goods on belt conveyors, which are based on the utilization of light of the UV to infrared range, sofar are not marketed in a commercial way.

From literature methods and devices are known, which use light beams of a defined wavelength to observe various matter, as e.g. country rock and coal in a mine, or individual components of goods on belt conveyors, as e.g. diamonds in ore from diamantiferous orebodies, or even tomatoes, and to provide information for directing, splitting or blending of material.

The German patent DD 293 748 A5 of the Martin-Luther-Universität, Halle-Wittenberg of the year 1990 describes a "Verfahren und Vorrichtung zum Sortieren von Tomaten nach ihrem Reifegrad" (Method and Device for Sorting Tomatoes According to Their Ripeness). The use of a light source with a defined wavelength for the irradiation of tomatoes is disclosed, which depending on their respective degree of ripeness display photoluminescence of different intensity.

The published patent application DE 38 18 588 A1 of "Bergwerksverband GmbH", Essen, Germany of the year 1988 desribes a "Verfahren und Anordnung zur Unterscheidung unterschiedlicher Materialien" (Method and Device for Differentiation Between Different Matter). Here the use of one or various systems for irradiation and observation at defined excitation wavelengths and defined wavelength bands for observation to differentiate for example between coal and country rock is mentioned.

The two patent applications GB 2 219 079 A and GB 2 219 082 A by the company "Gersan Establishment" of Liechtenstein of the year 1989 disclose devices for concentrating diamantiferous ore, where the devices are specified having one light source operating at one defined wavelength and two or more receiver systems.

Already in the year 1980 the Canadian company "Scintrex Limited" of Concord, Ontario in the British patent GB 2 089 029 A gave a detailed description of a "Method and Apparatus for the Remote Detection of Certain Minerals of Uranium, Zinc, Lead and Other Metals". Here also one light source with one emitted wavelength or, for a multi-channel system, various light sources with one defined wavelength each for the excitation of photoluminescence are mentioned.

The Australian company CSIRO, "Commonwealth Scientific and Industrial Research Organisation", in 1989 applied for the U.S. Pat. No. 4,959,549 "Determination of Properties of Coal". The surface of coal on a belt conveyor is irradiated with UV light and the intensity of the photoluminescence is measured. A comparison of the measured signals with reference data leads to the determination of relevant properties of the coal. In this application also one light source with one defined wavelength is to be used.

It is known, that the intensity of photoluminescence depends on the wavelength of the excitation. These relationships are described in BROICHER, H. F., 1987, "Naturwissenschaftliche, technische und wirtschaftliche Aspekte bei der Entwicklung und Nutzung eines Photolumineszenz-Sensors für die Rohstoffprospektion" (Scientific, Technical and Economic Aspects for Designing and Operating a Photoluminescence Sensor for Prospecting for Raw Materials), Verlag von Dietrich Reimer in Berlin, Germany.

Therefore, for the precise determination of individual minerals or the alteration of the composition of a mixture of minerals it is desirable to operate at various wavelengths when exciting photoluminescence. Furthermore it is known, that the absorption and reflection at distinct wavelengths as well as the thermal inertia of minerals can be utilized for their respective determination.

According to the state-of-the-art, for each specific wavelength one light source is required, the light source preferentially being a laser. If the material shall be irradiated at various distinct wavelengths, then various light sources are required. Such a device will become very demanding regarding costs, space and energy consumption.

SUMMARY OF THE INVENTION

It is the objective of the present invention to provide a device of said kind that is capable of observing the bulk goods on a belt conveyor and of detecting quality alterations of bulk goods by means of excitation of photoluminescence, by irradiation at a wavelength with specific reflectance and by thermal irradiation.

It is the basic idea of the present invention in contrast to prior art devices,
  not to equip the device with a laser as the source of light, which directly irradiates the material with monochromatic light, so that for multi-channel systems various lasers have to be installed,
  but to produce with only one laser as the source of light various simultaneous light beams at different wavelengths by means of frequency multipliers and, thus, to measure and analyze the photoluminescence typical for the bulk goods or for one component of the bulk goods after excitation at a suitable wavelength, the photoluminescence after excitation with a wavelength different from the first wavelength land less effective and/or the reflectance of this irradiation and the thermal inertia or absorption of infrared light.

Bulk goods transported on belt conveyors generally are minerals as for example limestone, phosphate ore, iron ore, uranium ore, potash, rock salt, ores of the non-ferrous metals, ores of the rare earths, beach sands with heavy minerals, hard coal, lignite and oil shales.

All these materials and also mixtures of these as well as country rock mined exhibit a photoluminescence signal, either inherent or caused by contamination, when properly excited. It is known that some minerals' photoluminescence is short lived, that is, the decay time of fluorescenmce is less than 200 nanoseconds (nsec). To measure and analyse such a short signal the excitation or at least the extinction of the excitation has to happen in a very short time of a few nanoseconds only. A pulsed laser is a suitable source of light.

An especially suited laser for the present objective of material testing is a Nd:YAG laser emitting at a wavelength of 1,064 nm.

According to the present invention, a frequency multiplication beam will produce distinct wavelengths of 1,064, 532 and 266 nm. The UV light component at 266 nm is especially suited for excitation of photoluminescence in most minerals. The green light component at 532 nm also can excite photoluminescence in some minerals and will be evaluated in reflectance measurements. The infrared component facilitates thermal and reflectance measurements.

Selection of the specific wavelength for each channel is done by means of dichroic mirrors, which might also expand or focus the light beams, if already manufactured as concave or convex components. The use of a prism for the separation of the different light beam components also is possible.

If the material on the belt conveyor is irradiated and observed in various equidistant spots of identical size, triggering of the system depending on the speed of the belt conveyor is realized in such a way, that always the same areas of the material are irradiated by the various light beams and, consecutively, are observed. Thus it is achieved, that in continuous operation each area is irradiated by each distinct light beam and that the signals produced are received and evaluated.

BRIEF DESCRIPTION OF THE DRAWING

By means of the embodiment shown in the drawing the invention shall further be described.

The drawing shows schematically the preferred embodiment of the device in side elevation.

In the drawing a belt conveyor (7) is shown with the bulk goods on it. For irradiation of areas on the surface of the bulk goods with light at different wavelengths in the spots (6) there are arranged above the belt conveyor (7) a laser (1) and attached to it a frequency multiplier (2), mirrors (4) for deflection and dichroic mirrors (3) as well as lenses (5) for beam expansion. Furthermore, according to the number of spots (6) there are installed various detector systems with optical components to view the spots (6), filters (9) for selecting wavelength bands for evaluation and photodetectors (10). The electronic means for triggering the system and for analysis of the electric signals is not shown.

We claim:

1. A device for detecting variations in the quality of bulk goods during transport on a moving belt conveyor comprising:
   a) a pulsed monochromatic light source for producing a pulsed monochromatic light beam;
   b) a frequency multiplying means for frequency multiplying said light beam to produce a frequency multiplied light beam having a plurality of wavelengths;
   c) a selecting and deflecting means for selecting a plurality of light beams, each having a defined wavelength, from said frequency multiplied light beam, and for deflecting each of said selected light beams toward the moving belt conveyor carrying the bulk goods to be detected such that the belt conveyor is simultaneously irradiated at a plurality of defined regions arranged in the direction of conveyor movement;
   d) a detector means operatively associated with each of said defined regions for detecting electromagnetic energy emitted therefrom following irradiation, each of said detector means including a reflector, a filter and a photodetector; and
   e) a triggering means for controlling the pulse of said light source, said pulse being a function of belt conveyor speed whereby a designated portion of the bulk material is sequentially irradiated by each of said directed light beams as it travels along the belt conveyor.

2. Device according to claim 1, wherein said pulsed light source (1) is a laser.

3. Device according to claim 2, wherein said laser is emitting monochromatic light at a wavelength in the range of 230 to 1,200 nanometers (nm), said laser is a Nd:YAG laser, which emits at a wavelength of 1,064 nm.

4. Device according to claim 1, wherein said frequency multiplying means is a single frequency multiplier that doubles or quadruples the frequency of the monochromatic light or various frequency multipliers to produce multiplication of frequencies of the monochromatic light and, thus, light beams having multiple distinct wavelengths.

5. Device according to claim 1, wherein said frequency multiplying means is a single frequency multiplier that quadruples the frequency of the monochromatic light, thus generating from an incoming light source wavelength of 1,064 nm a beam with 532 nm and 266 nm, respectively.

6. A device as in claim 1 and wherein:
   a) said selecting and deflecting means includes a lens for expanding each of said deflected light beams.

7. A device as in claim 1 and wherein:
   a) said selecting and deflecting means includes a dichroic mirror.

8. A device as in claim 1 and further comprising:
   a) a beam expander means for expanding each of said deflected light beams.

9. A device as in claim 1 and wherein:
   a) said selecting and deflecting means includes a prism.

10. A device as in claim 1 and wherein:
    a) said frequency multiplied light beam having wavelengths selected from the group consisting of ultraviolet light, visible light and infrared light.

* * * * *